(12) United States Patent
Oberlin et al.

(10) Patent No.: US 9,945,826 B2
(45) Date of Patent: Apr. 17, 2018

(54) FUNCTIONAL TEST FOR GAS SENSORS

(71) Applicant: Mettler-Toledo AG, Greifensee (CH)

(72) Inventors: René Oberlin, Würenlos (CH); André Möbius, Zürich (CH)

(73) Assignee: Mettler-Toledo GmbH, Greifensee (CH)

( * ) Notice: Subject to any disclaimer, the term of this patent is extended or adjusted under 35 U.S.C. 154(b) by 777 days.

(21) Appl. No.: 14/468,671

(22) Filed: Aug. 26, 2014

(65) Prior Publication Data
US 2014/0360245 A1  Dec. 11, 2014

Related U.S. Application Data

(63) Continuation of application No. PCT/EP2013/054490, filed on Mar. 6, 2013.

(30) Foreign Application Priority Data

Mar. 12, 2012 (EP) .................................. 12159052

(51) Int. Cl.
*G01N 33/00* (2006.01)
*G01N 27/18* (2006.01)

(52) U.S. Cl.
CPC ......... *G01N 33/0006* (2013.01); *G01N 27/18* (2013.01)

(58) Field of Classification Search
CPC .................... G01N 33/0006; G01N 27/18
USPC ........................................................ 73/1.06
See application file for complete search history.

(56) References Cited

U.S. PATENT DOCUMENTS

| 5,144,831 | A | 9/1992 | Hale et al. |
| 5,255,553 | A | 10/1993 | Hale et al. |
| 2008/0245145 | A1* | 10/2008 | Mayer .................. G01F 1/6845 73/204.26 |

FOREIGN PATENT DOCUMENTS

| DE | 1002146 B | 2/1957 |
| DE | 4439715 A1 | 5/1996 |
| EP | 0348243 A2 | 12/1989 |
| EP | 0433741 A1 | 6/1991 |
| EP | 0501089 A1 | 9/1992 |

* cited by examiner

*Primary Examiner* — Daniel S Larkin
(74) *Attorney, Agent, or Firm* — Standley Law Group LLP

(57) ABSTRACT

A gas sensor which works according to the principle of thermal conductivity is functionally tested. In the method, a calibration cycle is conducted in which a membrane of the gas sensor is immersed in a fluid calibration medium having a known concentration of a target gas. After the calibration cycle, a measurement chamber of the gas sensor is purged with a purging gas. Then, a measuring cycle is conducted, using a thermal conductivity sensor to measure the target gas in the measurement chamber. Using a calibration baseline established from the calibration cycle and a measurement baseline in the measurement cycle, a baseline comparison value is obtained and compared to a predetermined baseline threshold value. An error message, indicating a malfunction in the purging gas supply, is generated when the baseline comparison value exceeds the predetermined baseline threshold value.

11 Claims, 3 Drawing Sheets

FUNCTIONAL TEST FOR GAS SENSORS

CROSS-REFERENCE TO RELATED APPLICATIONS

This application is entitled to benefit of a right of priority under 35 USC § 119 from PCT/EP2013/054490 of 6 Mar. 2013, which in turn makes a claim of priority to European patent application 12159052.5, filed on 12 Mar. 2012. The content of each of the foregoing is incorporated by reference as if fully recited herein.

TECHNICAL FIELD

The invention relates to a functional test for gas sensors which work according to the principle of thermal conductivity.

BACKGROUND

Gas sensors which work according to the principle of thermal conductivity can be used for the determination of gases or gaseous components in fluid media. "Fluid media" are understood here to mean both liquid and gaseous media. The gas to be detected or the gaseous component to be detected, also referred to in the following as "target gas", can be present in the medium as gas or in dissolved form, wherein the fluid medium can contain, apart from the target gas, further components or dissolved substances, such as solids, gases or liquids. Specific thermal conductivity parameters of the target gas are determined first, from which further parameters, such as for example the concentration, the pressure or the partial pressure of the target gas in the fluid medium, can be derived.

Gas sensors which work according to the principle of thermal conductivity are known, amongst others, from EP 0 501 089 A1, EP 0 429 397 A1, EP 0 433 741 or DE 4 439 715 A1.

The measurement principle is based on a combination of diffusion of a target gas through a membrane with subsequent detection of the target gas by means of a thermal conductivity measurement. The employed gas sensor comprises a membrane, which is brought into contact with the fluid medium for the measurement. This membrane separates the fluid medium from a measurement chamber in the gas sensor, in which a thermal conductivity sensor is disposed. The membrane comprises for example a polymer layer or polymer film which is permeable for the target gas and at the same time impermeable to liquid, so that only the target gas can pass through the membrane into the measurement chamber. The employed polymer has a permeability matched to the target gas.

The measurement chamber is purged with a purging gas before each measuring procedure in order to remove from the measurement chamber residues from a preceding sample of the target gas. The purging gas should have a thermal conductivity differing from the target gas and in addition be chemically inert with respect to the target gas and/or the materials of the sensor, i.e. should not react with these substances.

Following this purging procedure, the target gas can again penetrate through the membrane into the measurement chamber. At least one time-dependent thermal conductivity parameter is measured with the thermal conductivity sensor, which is related to the concentration of the target gas in the measurement chamber and therefore in the fluid medium. By taking account of the membrane permeability for the target gas, the partial pressure of the target gas can then be determined from this parameter and its concentration in the fluid medium can be determined therefrom.

In addition, the gas sensor can be calibrated, as disclosed for example in EP 0 348 243 A1.

Gas sensors which work according to the principle of thermal conductivity are used in various industrial processes and process plants as well as in the laboratory. The possible uses range from $CO_2$ determination in beverage production to $N_2$, $H_2$ or $CO_2$ determination in biological processes and bioreactors. Further target gases that can be determined with such gas sensors are, for example, sulphur dioxide ($SO_2$) or hydrogen sulphide ($H_2S$).

Especially for the use in industrial plants, it is important that the gas sensors deliver reliable and reproducible results of constant quality.

As has been shown, the functional capability and therefore the reliability of the gas sensors are influenced by various malfunction states, such as faults in the purging gas supply and/or the penetration of moisture into the interior of the sensor.

The malfunction states lead to faulty measurements and can even lead to failure of the gas sensor.

The problem thus arises of providing a method for the functional testing of a gas sensor which works according to the principle of thermal conductivity, in order to detect malfunction states of the gas sensor already during operation and in particular on-line.

SUMMARY

This problem is solved by a method for the on-line functional testing of a gas sensor which works according to the principle of thermal conductivity. The gas sensor comprises a measurement chamber with a purging gas connection, a thermal conductivity sensor disposed in the measurement chamber for determining one or more measurement values, a temperature sensor and a membrane, which separates the measurement chamber from a fluid medium during operation and is permeable for a target gas. The method for the functional testing of the gas sensor comprises a plurality of steps.

A calibration cycle is first carried out in a calibration medium and a calibration baseline is determined. The calibration medium is a fluid medium with a known concentration of the target gas. A calibration cycle comprises at least a purging procedure and a measuring procedure. During a measuring procedure and/or a purging procedure, at least one measurement value can be detected with the thermal conductivity sensor and a corresponding calibration baseline can be determined therefrom.

A measurement cycle is then carried out in a measurement medium and a corresponding measurement baseline is determined from the obtained measurement values. The measurement medium is a fluid medium with an unknown concentration of a target gas. A measurement cycle comprises at least a purging procedure and a measuring procedure, which are carried out after one another. A purging procedure is carried out before or following the measuring procedure in order to record measurement values or a series of measurement values, so that the measurement chamber is essentially free from residues at the start of a measuring procedure.

The measurement chamber is purged with a purging gas in a purging procedure and possible residues are thus removed from the measurement chamber. A measuring procedure can then be carried out, wherein the membrane of the gas sensor is brought into contact with a fluid medium, so that target gas contained in the fluid medium can diffuse through the membrane into the measurement chamber. Purging gas present in the measurement chamber mixes with the target gas or is displaced by the latter. One or more measurement values can be determined with the thermal conductivity sensor disposed in the measurement chamber. The measurement values can be detected at preselected points in time, at preselected time intervals or continuously.

A calibration or measurement baseline can be determined from a plurality of measurement values determined as a function of time during a calibration or measurement cycle. By taking account of the calibration baseline and measurement baseline, a baseline comparison value can be determined, which is then compared with a preselected baseline threshold value. If the amount of the baseline comparison value is greater than the baseline threshold value, a first error message is generated. The first error message indicates a malfunction in the purging gas supply.

Surprisingly it has been shown, that an indication of a malfunction of the purging gas supply can already be obtained by means of a baseline comparison between a calibration cycle and a measurement cycle, so that the purging gas supply can be checked manually or automatically. The measurement voltage as a function of the voltage values determined during the purging procedure is referred to here as the baseline. For the calibration baseline, use is made of the baseline values determined during the calibration procedure, said baseline values being a function of the voltage values determined during the purging procedure within the calibration procedure. For the measurement baseline, use is made of the baseline values determined during the measuring procedure, said baseline values being a function of the voltage values determined during the purging procedure within the measuring procedure. The malfunction can also be displayed to the user, for example as an electronic, acoustic and/or optical signal. Measurement values with a high degree of reproducibility and a high quality can be generated in this way.

The method can also comprise steps with which it can be verified whether moisture has penetrated into the measurement chamber, which leads to the generation of one or more further error messages. The measurement values can be falsified by the penetration of moisture into the measurement chamber.

For this purpose, a measurement cycle is carried out in a measurement medium, said cycle comprising a purging procedure and a measuring procedure. During the measuring procedure, a measurement voltage is detected with an electronic measurement circuit of a gas sensor, which represents a measure of the thermal conductivity to be measured. This measurement voltage is compared with a preselected voltage range. If the measurement voltage lies outside the preselected voltage range, a further error message is generated. If the measurement voltage lies inside the preselected voltage range, a measurement current value can also be determined from the voltage drop across the measuring resistor or across the corresponding shunt resistor of the measurement circuit. A first control value is determined by comparing the measurement current value with a preselected measurement current value. A control current value is also determined via a control circuit. The measurement circuit comprises the control circuit. The control current value is determined from the voltage drop across the corresponding shunt resistor of the control circuit. A second control value can be determined by comparing the measurement current value with the control current value.

The first and/or the second control value can then be compared with a first control threshold value. If the first and/or the second control value is greater than the control threshold value, a second error message is generated, which indicates a malfunction of the gas sensor on account of moisture that has penetrated into the measurement chamber.

This method can also include a comparison of the second control value with a second control threshold value, if the second control value is greater than the first control threshold value. If the second control value is greater than the first and greater than the second control threshold value, a third error message can be generated, which indicates a failure of the gas sensor on account of moisture that has penetrated into the measurement chamber.

The moisture that has penetrated into the measurement chamber can be determined alternatively or additionally by the following method steps and can be displayed to the user. For this purpose, a measurement cycle is carried out in a measurement medium and a measurement voltage is determined during the measuring procedure with an electronic measurement circuit of the gas sensor. A measurement current value is then determined from the voltage drop across the measuring resistor or across the shunt resistor of the measurement circuit. By readjusting an adjustable resistor or the supply voltage of the electronic measurement circuit, the measurement current value can be matched to a preselected measurement current value. The change in the adjustable resistor or the supply voltage required for this is determined as the value of a manipulated variable. This value of the manipulated variable is then compared with a preselected first value of a control manipulated variable. If the value of the manipulated variable is greater than the value of the control manipulated variable, a second error message can be generated which indicates a malfunction of the gas sensor.

Furthermore, a comparison of the value of the manipulated variable with a second value of the control manipulated variable can also be carried out if the value of the manipulated variable is greater than the first value of the control manipulated variable. If the value of the manipulated variable is greater than the first and greater than the second value of the control manipulated variable, a third error message can be generated, which indicates a failure of the gas sensor on account of moisture that has penetrated into the measurement chamber.

A further aspect of the method according to the invention concerns the checking of the membrane of the gas sensor. The membrane closes off the measurement chamber of the gas sensor against the fluid medium and in addition is permeable for the target gas. The membrane is therefore semi-permeable and has a defined permeability. If the permeability of the membrane changes, for example if the membrane has mechanical faults, such as tears or holes, or if the membrane is defective, for example on account of changed pore sizes, then this has a direct influence on the measurement results. The measurement results can be falsified by a defective membrane, because, apart from the target gas, interfering components can for example pass into the measurement chamber or the diffusion of the target gas into the measurement chamber can be hindered or greatly increased. It is therefore desirable that the functional capability of the membrane of a gas sensor is also checked, in particular on-line.

For this purpose, a measurement cycle can be carried out with a gas sensor which works according to the principle of thermal conductivity and the measurement voltage can be determined as a function of time during the measuring procedure. The time-related behavior of the measurement voltage during the measuring procedure can then be compared with a preselected first membrane threshold value range. During a following purging cycle, a purging measurement voltage can be determined during the measuring procedure of the purging cycle and the time-related behavior of the purging measurement voltage can be compared with a preselected second membrane threshold value range.

If both voltages, the measurement voltage and the purging measurement voltage, lie outside their respective threshold value ranges, the first membrane threshold value range and the second membrane threshold value range, a fourth error message can be generated, which indicates a malfunction of the membrane in the gas sensor.

The user can thus already be informed during the ongoing operation of the gas sensor about problems with the membrane and/or a defective membrane and can take measures for replacement of the membrane or of the gas sensor.

The first, second, third and/or fourth error message can be recorded in a control unit of the gas sensor. Furthermore, the first, second, third and/or fourth error message can be displayed to the user electronically, optically and/or acoustically.

An error message recorded in the control unit of the gas sensor can for example create an identification of measurement values determined with a defective membrane, so that the latter are not taken into account in a subsequent evaluation, or even bring about a shutdown of the gas sensor. In addition, the user can already be informed about a malfunction of the gas sensor during the ongoing operation of the gas sensor and can take or initiate measures to remove the malfunction, for example the replacement of components, such as the membrane, the checking and changing of adjustments of the purging gas supply, the replacement of seals and/or the replacement of the entire gas sensor.

A gas sensor for performing the method according to the invention for the on-line functional testing comprises a measurement chamber with a purging gas connection, a thermal conductivity sensor disposed in the measurement chamber for determining one or more measurement values, and a membrane which separates the measurement chamber from a fluid medium during operation and is permeable for a target gas which is present in the fluid medium, wherein at least a first, second and/or third error message can be generated by the gas sensor during the performance of a purging cycle and/or a measurement cycle, said error message indicating at least one malfunction of the gas sensor on account of a defective purging gas supply, penetrated moisture and/or the membrane.

Furthermore, the gas sensor can comprise a control unit, which is disposed completely or partially in a sensor body of the gas sensor, wherein the control unit records and/or processes the first, second, third and/or fourth error message.

The control unit also comprises a control circuit, which can detect leakage currents which arise due to moisture that has penetrated into the sensor body.

BRIEF DESCRIPTION OF THE DRAWINGS

Various examples of embodiment of a method according to the invention and a gas sensor suitable for performing the method are described in detail with the aid of the following Figures, wherein the same elements are provided with the same or similar reference numbers. The Figures show.

DETAILED DESCRIPTION

Figure 1:
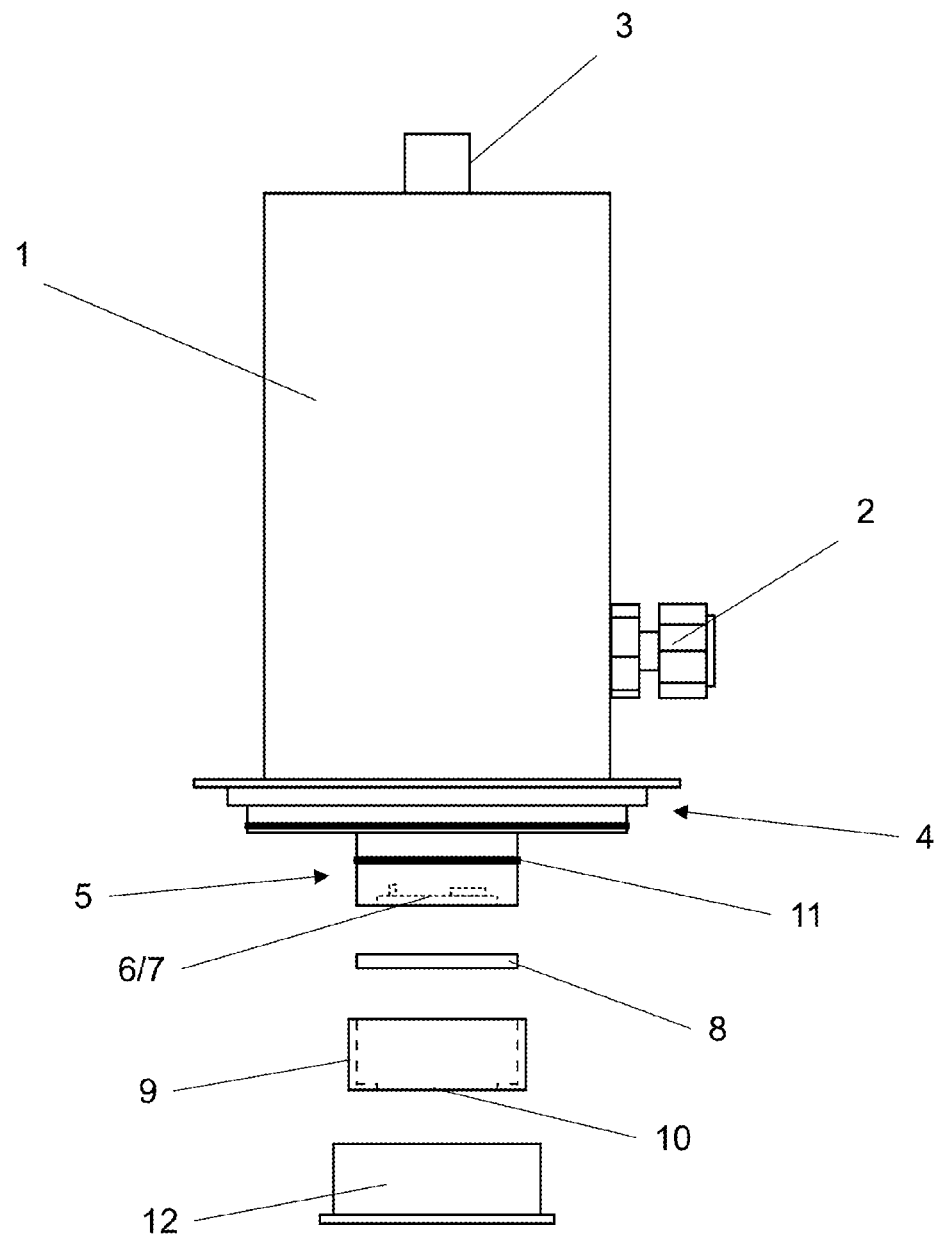
FIG. 1 is an exploded representation of a gas sensor which works according to the principle of thermal conductivity.

FIG. 1 shows a schematic exploded representation of a gas sensor working according to the principle of thermal conductivity. The gas sensor comprises a sensor body 1, which comprises a purging gas connection 2 and a connection 3 for connecting the gas sensor to a transmitter and/or a process control point. Disposed in the sensor body 1 are, amongst other things, the measurement electronics and the control electronics as well as the associated circuits, which cannot be seen here. At its medium-side end, which is in contact with a fluid medium during operation, the gas sensor comprises a flange 4 for the connection of the gas sensor to a container. Furthermore, a measuring connection piece 5 projecting into the fluid medium during operation can be seen at the medium-side end of the gas sensor, in which measuring connection piece a measurement chamber 6 with a thermal conductivity sensor 7 is disposed, see also FIG. 2.

Measurement chamber 6 is covered by a membrane 8, which is fastened to measuring connection piece 7 with a cap 9. Cap 9 comprises an opening 10, through which fluid medium 13 can enter into contact with membrane 8. The composition and the structure of membrane 8 are adapted to the target gas of interest. Membrane 8 can be made for example of a ceramic material, a composite material and/or a polymer material. A membrane 8, which is suitable in particular for the $CO_2$ measurement, can be made for example of a composite material which comprises a polymer film, such as PTFE, which is fixedly connected for mechanical reinforcement to a suitable rigid grid structure, such as a metal netting. In addition, a seal 11, here in the form of an O-ring, is disposed between cap 9 and measuring connection piece 7, in order to seal measurement chamber 6 with respect to the liquid medium.

For storage or transport, measuring connection piece 5 and in particular membrane 8 can also be protected with a cover 12.

Figure 2:
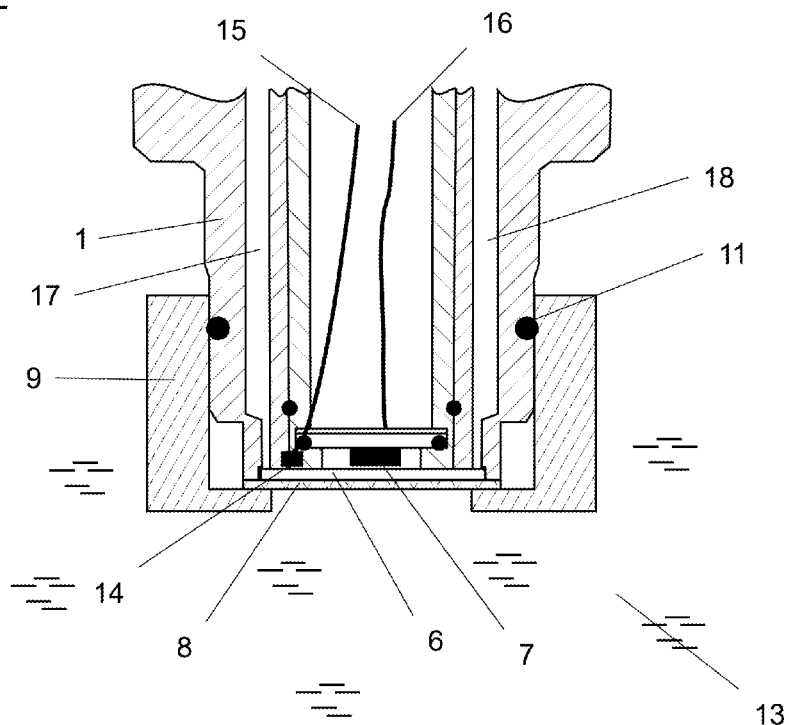
FIG. 2 is a very schematic cross-sectional drawing through the measurement connecting piece of a gas sensor.

FIG. 2 shows very schematically a cross-section through measuring connection piece 5 in the assembled state of the gas sensor without a cover. As can be seen here, measuring connection piece 5 dips during operation into fluid medium 13, which is disposed in a suitable container. A target gas is present in fluid medium 13, said target gas being dissolved in fluid medium 13 or mixed with the latter. The target gas can penetrate through membrane 8 into measurement chamber 6, since membrane 8 is selectively permeable for the target gas.

Disposed at the bottom of measurement chamber 6 is a thermal conductivity sensor 7 and a temperature sensor 14, which are each connected to the control unit disposed in the gas sensor via lines 15, 16, which are only indicated here. A temperature compensation of the measurement value determined by thermal conductivity sensor 7 can be carried out via the temperature determined with temperature sensor 14.

Furthermore, measurement chamber 6 comprises a gas supply line 17 and a gas outlet 18. Via gas supply line 17, measurement chamber 6 can be flooded with a purging gas in order to remove residues from measurement chamber 6. The purging gas and/or the target gas to be expelled can escape out of measurement chamber 6 via gas outlet 18. Gas outlet 18 also ensures that a pressure build-up in measurement chamber 6 is prevented.

Figure 3:
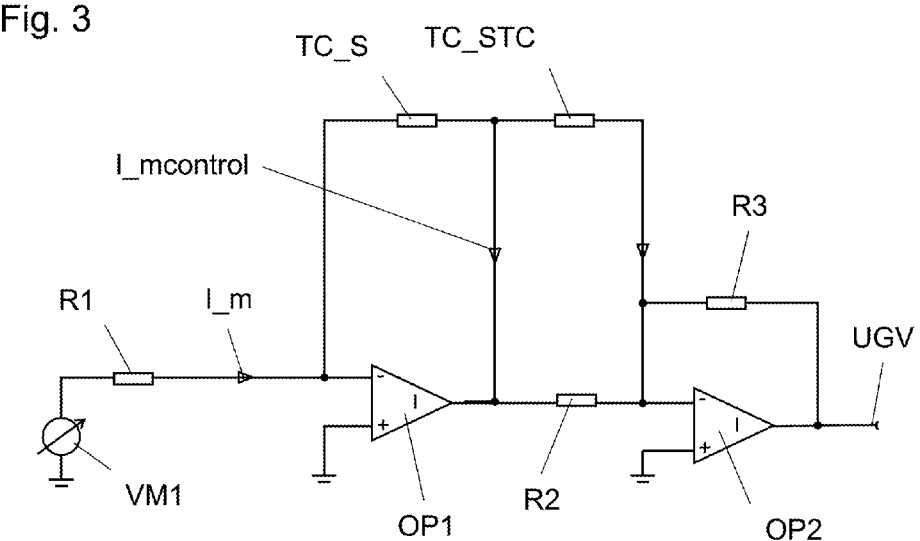
FIG. 3 is a very simplified circuit diagram of a gas sensor with a control circuit for checking leakage currents.

FIG. 3 shows a very simplified circuit diagram of an electronic measurement circuit of the gas sensor with a control circuit.

The gas sensor is supplied with a constant supply current I_m, which is fixedly preselected for the given measurement value determination. Current I_m is adjusted by a preset supply voltage VM1 and a variable resistor R1.

Furthermore, current I_m can also be adjusted as part of the control circuit in order to check the functioning of the gas sensor on-line. In this case, the measurement circuit comprises either an adjustable resistor R1 or an adjustable supply voltage VM1.

This constant supply current I_m enables the determination of resistance TC_S of the thermal conductivity sensor via the output voltage of a first operational amplifier OP1, said determination being important for the measurement. The output voltage of first operational amplifier OP1 is on the one hand temperature-compensated and on the other hand amplified by means of a further circuit part with a second resistor R2 and the temperature sensor, referred to here as resistance TC_STC, as well as a third resistor R3 and a second operational amplifier OP2. The output voltage of second operational amplifier OP2 is the actual measurement voltage UGV which is proportional to the thermal conductivity to be measured.

Calibration and measurement cycles can be carried out with the gas sensor, wherein each cycle in each case comprises at least a purging procedure and a measuring procedure. A calibration cycle is carried out in a calibration medium with a known target gas concentration and a measuring procedure is carried out in a measurement medium with an unknown target gas concentration as a fluid medium.

The measurement chamber is first purged with a suitable purging gas, this purging procedure being able to be carried out one or several times. The gas sensor, in particular the measuring connection piece, is then brought into contact with the corresponding fluid medium. The target gas contained in the fluid medium diffuses through the membrane into the measurement chamber, where the thermal conductivity in the measurement chamber is determined as a measurement value by means of the thermal conductivity sensor. The measurement values can be detected during a measuring procedure as single values, at preselected time intervals or continuously. Temperature-compensated measurement values can be determined on the basis of temperature values determined with the temperature sensor. As a purging gas, use may be made of various gases which include, amongst others, compressed air, nitrogen ($N_2$), carbon dioxide ($CO_2$) or a noble gas, such as argon or helium. The selection of the purging gas is influenced, amongst other things, by the composition of the measurement medium, for example the presence of interfering gases, and/or by the target gas to be determined.

Figure 4:
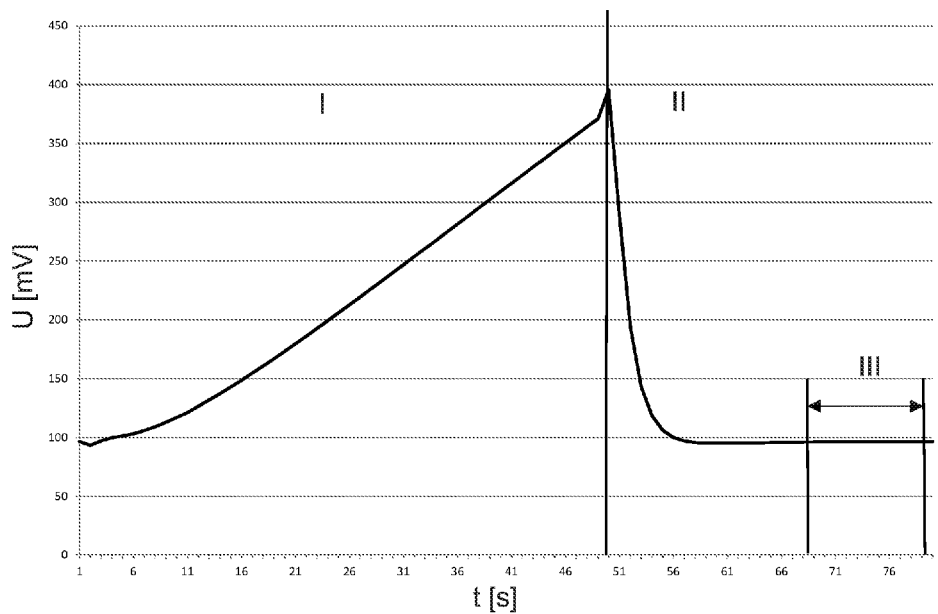
FIG. 4 is a voltage-time diagram for a typical calibration and measurement cycle for determining a baseline.
Figure 5:
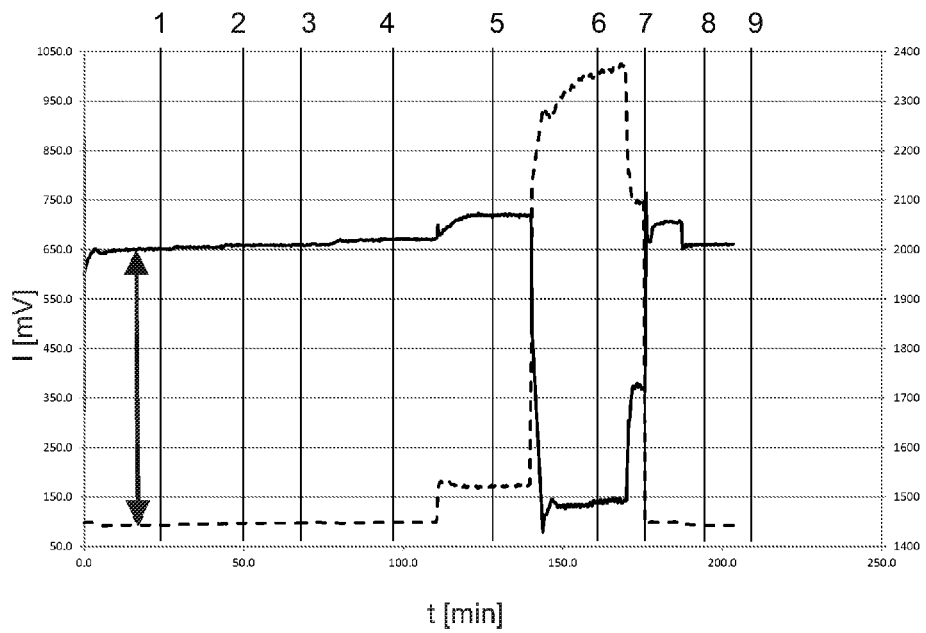
FIG. 5 is a diagram which shows the measured $CO_2$ partial pressure and the determined baseline as a function of the purging gas flow and time.

Examples of the implementation of the method according to the invention are shown in FIGS. 4 and 5.

FIG. 4 shows a typical voltage-time curve of the measurement voltage of a measurement or calibration cycle. The curve was detected with a $CO_2$ gas sensor according to the invention in pure $CO_2$ gas as a measurement medium and air as a purging gas. During measuring procedure I, the target gas diffuses out of the fluid medium into the measurement chamber, so that the concentration of the target gas in the measurement chamber increases with time and also therefore the detected thermal conductivity, which is proportional to the shown measurement voltage UGV. After completion of the measuring procedure, which here includes a number of measurement values, a purging procedure II is initiated, in which the purging gas is conveyed through the measurement chamber and the target gas is thus expelled out of the measurement chamber. The measurement chamber can be purged, for example, until such time as the measurement values of the thermal conductivity sensor are essentially stable. The baseline can then be determined by taking the average over the detected measurement voltage UVG in region III of the curve. Region III comprises here the last four seconds of the purging procedure of a calibration measurement cycle, in which the gas sensor delivers essentially stable measurement values. If the gas sensor is in contact with a calibration medium, a calibration baseline can thus be determined or, if the gas sensor is in contact with a measurement medium, a measurement baseline can be determined. The baseline comprises the calibration or measurement voltage as a function of the voltage values determined during the purging procedure.

FIG. 5 shows the time-related behavior of the baseline characteristic as a function of the purging gas flow. The measurements were detected with a $CO_2$ gas sensor according to the invention with air as a purging gas. Pure $CO_2$ gas with a $CO_2$ partial pressure of approx. 2000 mbar was used as a measurement medium. During the measurement, the purging gas flow is reduced from approx. 70 ml/min to approx. 0.2-0.5 ml/min and is then increased again to the initial value. The various purging gas flows are denoted with vertical lines in the diagram, wherein the following purging gas flows for example were determined: 1: 70 ml/min, 2: 50 ml/min, 3: 30 ml/min, 4: 10-20 ml/min, 5: 1-5 ml/min, 6: 0.2-0.5 ml/min, 7: 0.3-1.2 ml/min, 8: 3-14 ml/min, 9: 70 ml/min.

The measurement baseline curve, represented here as a discontinuous line, first shows the value of a calibration baseline of approx. 93 mV determined during a calibration cycle, with an optimum purging gas flow of approx. 70 ml/min. The double arrow indicates the point in time at which the sensor is calibrated and the calibration baseline is detected. In the course of the measuring procedure, the purging gas flow is disrupted by the latter being reduced, in order to simulate a defective purging gas supply. Even deviations in the purging gas flow of approx. 1 to approx. 5 ml/min lead to significant deviations in the $CO_2$ measurement value, which as a $CO_2$ partial pressure is represented as a continuous curve. The unfavorable change in the purging gas flow can also be read off on the curve of the measurement baseline, since the latter increases by approx. 80 mV to approx. 173 mV already with a purging gas flow reduced to approx. 10-20 ml/min (line 4). A further reduction of the purging gas flow to approx. 0.2 to approx. 0.5 ml/min (line 6), which essentially corresponds to a purging gas interruption, leads to an increase of the measurement baseline to approx. 990 mV and at the same time to a dramatic decline of the $CO_2$ measurement value. As soon as the purging gas flow was adjusted again to the initial optimum value of approx. 70 ml/min (line 9), it can be seen in the diagram that the values of the measurement baseline and also of the measured $CO_2$ partial pressure again correspond to the initial values.

A malfunction of the gas sensor on account of a faulty or deficient purging gas supply can thus be determined with the aid of the method described above, in which a baseline threshold value for the deviation of the measurement baseline from the calibration baseline of approx. 50 mV is established. The value of the baseline threshold value can easily be determined, as shown here, for any type of sensor and/or any target gas. After detection of the defective purging gas supply, the measurement can be continued after the purging gas supply has been checked and adapted.

Although the invention has been described by the presentation of specific examples of embodiment, it is obvious that numerous other variants of embodiment can be created in the knowledge of the present invention, for example by combining the features of the individual examples of embodiment with one another and/or exchanging individual functional units of the examples of embodiment.

What is claimed is:

1. A method for functionally testing a gas sensor operating according to the principle of thermal conductivity, the gas sensor designed to sense the presence of a target gas in a fluid medium, the gas sensor comprising a measurement chamber with a connection to a supply of a purging gas, a thermal conductivity sensor, disposed in the measurement chamber, configured for determining one or more measurement values, a temperature sensor, and a membrane that separates the measurement chamber from the fluid medium during operation, the membrane being permeable to the target gas; the method comprising the steps of:
    performing a calibration cycle, comprising the steps of:
        immersing the membrane of the gas sensor in a calibration medium that is a fluid medium with a known concentration of the target gas;
        conducting a purging procedure, comprising purging the measurement chamber with the purging gas;
        conducting a measuring procedure after the purging procedure, the measuring step comprising the step of using the thermal conductivity sensor to take a plurality of measurements of the gas in the measurement chamber, obtaining a plurality of time-related measurement voltage values; and
        determining a calibration baseline from the plurality of time-related measurement voltage values, the calibration baseline determined from a calibration voltage which is a function of the measurement voltage values determined during the purging procedure;
    performing a measurement cycle, comprising the steps of:
        immersing the membrane of the gas sensor in a measurement medium that is a fluid medium with an unknown concentration of the target gas;
        conducting a purging procedure, comprising purging the measurement chamber with the purging gas;
        conducting a measuring procedure after the purging procedure, the measuring step comprising the step of using the thermal conductivity sensor to make a plurality of measurements of the gas in the measurement chamber,
        obtaining a plurality of time-related measurement voltage values; and
        determining a measurement baseline from the plurality of time-related measurement voltage values, the measurement baseline determined from a measurement voltage which is a function of the measurement voltage values during the purging procedure;
    calculating a baseline comparison value taking account of the calibration baseline and the measurement baseline; and
    comparing the baseline comparison value to a predetermined baseline threshold value, and, if the baseline comparison value is greater than the baseline threshold value, generating a first error message, indicating a malfunction in the purging gas supply.

2. The method of claim 1, further comprising the steps of:
    during the measuring procedure of the measuring cycle, using an electronic measurement circuit of the gas sensor to determine a voltage; and
    comparing the determined voltage to a predetermined voltage range; and
    based upon the result of the comparing step, taking at least one of the following steps:
        generating a further error message if the determined voltage lies outside the voltage range;
        determining a measurement current value if the determined voltage lies within the voltage range, and comparing the determined measurement current value to a predetermined measurement current value to obtain a first control value;
        determining a control current value by means of a control circuit which is a part of the measurement circuit, and comparing the determined measurement current value to the determined control current value to obtain a second control value;
        comparing the first control value to a first control threshold value and comparing the second control value to a second control threshold value, and
        generating a second error message, which displays a malfunction of the gas sensor if, at least one of:
            the first control value is greater than the first control threshold value; or
            the second control value is greater than the second control threshold value.

3. The method of claim 2, further comprising the steps of:
    comparing the second control value to a predetermined third control threshold value if the second control value is greater than the predetermined second threshold value; and
    generating a third error message, indicating a failure of the gas sensor, if the second control value is greater than the third control threshold value.

4. The method of claim 1, further comprising the steps of:
    during the measurement procedure of the measurement cycle, using an electronic measurement circuit of the gas sensor to determine a measurement voltage;
    determining a measurement current value;
    adjusting the measurement current value to correspond to a predetermined measurement current value, thereby determining a value of a manipulated variable, by adjusting at least one of: an adjustable first resistor or the supply voltage of the electronic measurement circuit; and
    comparing the value of the manipulated variable to a predetermined first value of a control manipulated variable and generating a second error message, indicating a malfunction of the gas sensor, if the value of the manipulated variable is greater than the predetermined first value of the control manipulated variable.

5. The method of claim 4, further comprising the steps of:
    comparing the value of the manipulated variable to a predetermined second value of the control manipulated variable if the value of the manipulated variable is greater than the first value of the control manipulated variable; and
    generating a third error message, indicating a failure of the gas sensor, if the value of the manipulated variable is greater than both the first and the second values of the control manipulated variable.

6. The method of claim 1, further comprising the steps of:
during a measurement procedure of the measurement cycle, using an electronic measurement circuit of the gas sensor to determine, as a function of time, a plurality of measurement voltages;
comparing the time-related behavior of the measurement voltage to a predetermined first membrane threshold value range;
performing a purging procedure to determine, as a function of time, a plurality of purging measurement voltages during the purging procedure;
comparing the time-related behavior of the purging measurement voltage to a preselected second membrane threshold value range; and
generating a fourth error message, indicating a malfunction of the membrane in the gas sensor, if the measurement voltage lies outside the first membrane threshold value range and the purging measurement voltage lies outside the second membrane threshold value range.

7. The method of claim 1, wherein:
any error message generated is recorded in a control unit of the gas sensor.

8. The method of claim 7, wherein:
any error message generated is displayed in at least one of the following means: optically, acoustically and electronically.

9. A device for sensing the presence of a target gas in a fluid medium, the device comprising:
a measurement chamber having a connection for a purging gas;
a temperature sensor, disposed in the measurement chamber;
a thermal conductivity sensor, disposed in the measurement chamber to determine one or more measurement values;
a membrane, permeable to the target gas, arranged to separate the measurement chamber from the fluid medium during operation, and
a control unit, in communication with the thermal conductivity sensor, programmed with an algorithm perform the method of claim 1 to generate at least one error message to indicate at least one malfunction of the device.

10. The device of claim 9, further comprising:
a sensor body, with the control unit, at least partially disposed therein.

11. The device of claim 10, wherein:
the control unit comprises a control circuit that detects leakage currents arising from moisture that has penetrated into the sensor body.

* * * * *